United States Patent [19]

Goodwin et al.

[11] 4,340,615

[45] Jul. 20, 1982

[54] APPARATUS FOR ANALYSIS OF ABSORBED GASES

[75] Inventors: Brian Goodwin, Cheshire; Peter Middleton, London, both of England

[73] Assignee: The Medishield Corporation Limited, London, England

[21] Appl. No.: 155,912

[22] Filed: Jun. 3, 1980

[30] Foreign Application Priority Data

Jun. 7, 1979 [GB] United Kingdom ................ 7919942

[51] Int. Cl.³ .............................................. A61B 5/00
[52] U.S. Cl. ..................................... 427/2; 128/635; 128/632; 128/768; 204/195 B
[58] Field of Search ....................... 427/2; 204/195 B; 128/635, 768, 632; 55/158

[56] References Cited

U.S. PATENT DOCUMENTS 3,658,053 4/1972 Fergusson ........................... 128/632
3,717,525 2/1973 Bultemam ............................ 55/158
3,969,548 7/1976 Hunter ................................. 55/158
4,230,463 10/1980 Henis ................................... 427/245
4,243,701 1/1981 Riley ................................... 55/188

FOREIGN PATENT DOCUMENTS 2003050 3/1979 United Kingdom .................. 55/158

Primary Examiner—Sam Silverberg
Attorney, Agent, or Firm—Roger M. Rathbun; Larry R. Cassett

[57] ABSTRACT

A device in the form of a flexible intravascular probe for use in analyzing absorbed blood gases includes a gas-permeable membrane 10 comprising two layers in intimate contact and supporting each other. The permeability of the second layer 6 is significantly less than that of the first 5, and provides the desired permeability of the membrane 10 as a whole. The first layer 5 provides the desired mechanical compatibility and other properties of the membrane 10.

4 Claims, 2 Drawing Figures

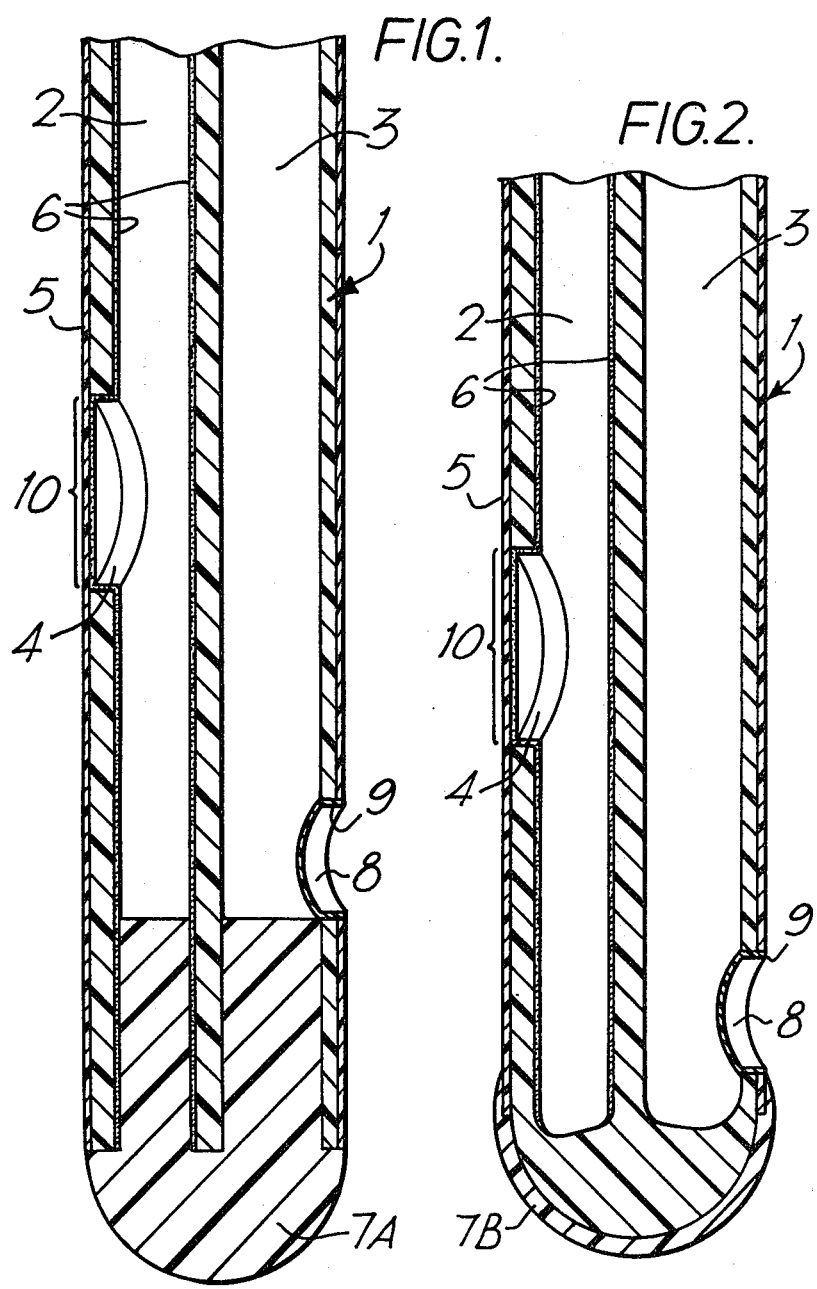

APPARATUS FOR ANALYSIS OF ABSORBED GASES

FIELD OF THE INVENTION

The present invention relates to a device for use in the analysis of absorbed gases in liquids and, in particular, is concerned with a flexible intravascular probe for use in the analysis of absorbed gases in the blood of man (or other mammals), e.g. by mass spectroscopy.

BACKGROUND OF THE INVENTION

In a known method for the continuous measurement of blood gases in vivo, use is made of an intravascular probe in the form of a flexible catheter having its distal end closed by a gas-permeable membrane. The said end of the probe is inserted into the blood vessel in question and its other end is connected to the inlet of a mass spectrometer whereby the device is evacuated. Gases absorbed in the blood diffuse through the membrane and pass along the catheter to the mass spectrometer wherein they are analysed.

U.S. Pat. No. 3,658,053 describes a blood catheter for use in the determination of the amount and type of dissolved gas in blood, which catheter includes a cannula of plastics material closed at one end. The cannula has an aperture in its wall towards said closed end, the exterior surface of at least that portion of the tube which includes the aperture being sheathed by a layer of gas-permeable material such as silicone rubber. Gases diffuse through the silicone rubber membrane and into the cannula via the aperture.

A constraint which has hitherto limited the practicability of known probes used in this procedure has been the need to manufacture the gas-permeable membrane from a bio-compatible material. Thus one known form of probe employs a flexible nylon catheter with a membrane of silicone rubber while another employs a malleable stainless steel catheter with a membrane of polytetrafluorethylene (PTFE). However, a disadvantage of silicone rubber as a membrane material is its inherently high gas permeability (typically in the region of $200 \times 10^{-10} \text{cm}^2\text{s}^{-1}(\text{cm Hg})^{-1}$ for oxygen at 20° C.) and the problem with a high permeability membrane is the tendency for the sampling region to become depleted of absorbed gas if the rate of transport of gas to the probe tip is not sufficiently high.

In other words the signal obtained from a probe of this type is undesirably dependent upon blood flow velocity. PTFE, on the other hand, is a virtually ideal membrane material from the standpoint of its inherent permeability. However, the problem with this material is the high temperature required for it to be worked, which precludes its use with flexible polymeric catheters. Thus, a PTFE membrane is limited to use with a catheter made from a material such as stainless steel, which does not however exhibit the same degree of flexibility as nylon for example. In particular the flexibility of stainless steel catheters is not sufficient to permit the safe monitoring of blood gas levels in infants.

Accordingly it is an aim of the invention to provide a form of construction for an intravascular probe or like device for use in the analysis of absorbed gases in liquids, whereby the above-discussed problems can be avoided.

SUMMARY OF THE INVENTION

According to one aspect of the present invention, a device for use in the analysis of absorbed gases in liquids comprises a flexible tube at or towards one end of which is provided a membrane across which gas can diffuse into the tube, in which the membrane comprises a first layer of gas-permeable material and a second layer of gas-permeable material in intimate contact with, and supported by, the first layer, and wherein the inherent gas permeability of the second layer is significantly less than the inherent gas-permeability of the first layer and, in use, defines the passage of gas across the membrane.

The device as defined above is particularly useful in the analysis of absorbed gases in blood, for example for in vivo measurements of oxygen and carbon dioxide gas tension in arterial and venous blood, but may be used in the analysis of absorbed gases in any liquid, eg, by mass spectroscopy or gas chromatography.

As advantage of the composite membrane construction of the device as hereinbefore defined is that the aforesaid second layer can be selected to provide a desired permeability for the membrane, in particular so that problems of gas-depletion and flow dependence are avoided, while the first layer can be selected to provide the desired mechanical compatibility and other properties of the membrane. The mechanical support afforded to the first layer by the second layer means that the second layer may itself be made thinner than known single-layer membranes with the result that an improved response time for the device may be achieved (response time being a function of the permeability of, and the square of the thickness of, the flow-defining level).

When the device is in the form of an intravascular probe the aforesaid first layer will generally constitute the outer layer of the membrane and be made of a recognised bio-compatible material, although this need not necessarily be so for the inner layer.

For use in the measurement of blood gas levels the permeability of the second layer of the membrane is preferably in the range $(0.001-0.01) \times 10^{-10} \text{cm}^2\text{s}^{-1}(\text{cm Hg})^{-1}$ for oxygen at 20° C.

In a preferred embodiment, the flexible tube is made from plastics material and closed at one end, the tube having an aperture in its wall towards said closed end, the exterior surface of at least that portion of the tube which includes the aperture being sheathed by a layer of bio-compatible gas-permeable material and the interior surface of that area of said sheathing layer which overlies said aperture being coated with a layer of gas-permeable material, the permeability of which is significantly less than that of the sheathing layer.

In this form of construction the gas-permeable membrane of the device is constituted by that portion of the sheathing material which overlies the tube aperture (ie, the said first layer of the membrane) together with that portion of the coating material supported thereby (ie, the said second layer of the membrane).

According to a second aspect of the present invention a method of manufacturing a device for use in the analysis of absorbed gases in liquids as hereinbefore defined, comprises the steps of: taking a flexible plastics material tube with an aperture in its wall; sheathing the exterior surface of at least that portion of the tube which includes said aperture with a layer of bio-compatible gas-permeable material; and coating the interior surface of that area of said sheathing layer which overlies said aperture with a layer of gas-permeable material, the permeability of which is significantly less than that of the sheathing layer.

It is a preferred feature of this form of construction that substantially the entire interior surface of the tube 5 receives the aforesaid coating of low permeability material. Such a coating helps to reduce the incidence of ambient gases diffusing through the walls of the tube and thereby increases the signal-to-background ratio achievable with the device. The coating can also act to reduce the ingress of water vapour from the walls of tubes made from hydrophilic materials (of which nylon is an example).

A further example of this coating is that an acceptable signal-to-background ratio can be achieved even with tubes made from materials of relatively high gas permeability which hitherto have been considered unsuitable for use as intravascular probes. In other words the tube material can be selected on considerations of its flexibility, bio-compatibility, durability or other characteristics; its inherent gas permeability need no longer be the principal criterion of selection.

A preferred material for the coating is polyvinylidene chloride propolymer (PVDC). An alternative is crystalline polytrifluorochloro-ethylene (kel-F).

BRIEF DESCRIPTION OF THE DRAWINGS

Embodiments of the invention will now be described, by way of example, reference being made to the Figures of the accompanying diagrammatic drawings in which:

FIG. 1 is a longitudinal cross-section through a device for use in the analysis of absorbed gases in liquids; and FIG. 2 is a longitudinal cross-section through a different device for use in the analysis of absorbed gases in liquids.

DESCRIPTION OF PREFERRED EMBODIMENT

Referring to FIGS. 1 and 2, each device is in the form of an intravascular probe and comprises a flexible bilumen catheter 1 made, for example, of nylon 6, the outside diameter of which may typically be 1.43 mm. A first lumen 2 is used as the gas sampling tube while the other lumen 3 is used as a blood (liquid) sampling tube.

As shown in the Figures, the outside wall of lumen 2 is somewhat thicker than that of lumen 3, and its cross sectional area is somewhat less than that of lumen 3. To manufacture the illustrated probes the following procedures are performed.

In each cas, a 50 cm length of the bilumen tubing is taken out at about 10 cm from one end an aperture 4 is cut in the outside wall of lumen 2. In prototype form the aperture is cut by means of a scalpel and guide. The guide consists of a short length of stainless steel tube having an aperture in its side such that when the bilumen tubing is placed into the guide the required size aperture can be cut in the tubing by following round the edge of the guide aperture with the scalpel. The aperture 4 typically measures 3 mm along the lumen axis by 0.52 mm, the lumen diameter.

Next an outer sheath 5 of medical grad silastic tubing is applied over the length of the bilumen tubing, using Analar grade Xylene to swell and lubricate the silastic. The Xylene is driven off using a hot air blower, causing the silastic to shrink onto the inner tubing. It is also ensured that any Xylene which may have entered the lumens is flushed out. The wall thickness of the sheath 5 is typically 25 microns.

The whole inner surface of the gas sampling lumen 2, including the area of the sheath 5 overlying aperture 4, is then given several coats of PVDC, to build up a layer 6 typically 6 microns thick. The PVDC coating is used in two forms—an organic solution and an aqueous latex. The latter is available ready to use, called IXAN (Registered Trade Mark) WA50, and marketed by LAPORTE Industries Limited. The organic solution is made by dissolving IXAN (Registered Trade Mark) WN 91 PVDC resin in tetrahydrofuran (THF) to a concentration of 200 g per kg of solution. The catheter tube is mounted vertically and 0.3 ml of the organic solution is injected into the top of the gas sampling lumen 2. Air is then passed through the lumen to flush out excess solution and drive off the solvent THF. The uniformity of the layer and to some extent the thickness is determined by the flow of air passing through the lumen. It has been found that a small flow rate, in the region of 1 ml s$^{-1}$, produces the best results. With air still passing through the lumen a hot air blower is used to heat the tubing to about 80° C. This procedure is then repeated three times using the aqueous base IXAN WA 50 latex.

Excess tubing is cut off each end leaving 1 cm before the aperture 4 and 25 cm after it. The distal end is then sealed by either of two methods. Firstly, as shown in FIG. 1, by drawing up in to both lumens 2 and 3 a quantity of medical grade silastic adhesive 7A, the plug so-formed then being fashioned into a hemisphere to ease the introduction of the probe into a blood vessel. Alternatively, as shown in FIG. 2, the end of the tubing may be heat sealed, followed by a dip coat 7B of medical grade silastomer. The latter method has proved to be the more acceptable in terms of smoothness of finish and ease of manufacture. The apparatus used for heat sealing may comprise a small block of PTFE heated with electrical resistance wire to about 90° C. A blind 1.5 mm diameter well is made in the PTFE block with a depth of approximately 3 mm by using a drill ground to obtain smooth surfaces and a hemispherical well bottom. The distal end of the bilumen tubing is placed into the heated well and by applying slight pressure the end is sealed.

Finally, an aperture 8 is cut in the outside wall and sheathing layer of lumen 3, for the taking of blood samples, and its edge painted with silastic elastomer 9 to prevent any possible gas leakage under the silastic sheath 5. The finished catheter is then put in a warm ventilated place for about 24 hours to allow the adhesives and elastomer to cure.

In use, the proximal end of the catheter (not shown) is provided with a bilumen adapter whereby the gas sampling lumen 2 can be connected to the inlet of a mass spectrometer or other analysis instrument, and blood sampling lumen 3 to a syringe.

In the construction of the probes shown in the Figures the gas-permeable membrane 10 is constituted by that portion of the silastic sheath 5 which overlies aperture 4 together with that portion of the PVDC layer 6 supported thereby. The silastic sheath 5 has a relatively high gas-permeability typically in the region of $200 \times 10^{-10}$cm$^2$s$^{-1}$(cm Hg)$^{-1}$ for oxygen, and serves essentially for the support and protection of the thin PVDC layer 6, having no significant effect on the rate of gas flow across the membrane. Rather it is the PVDC layer, typically having a gas permeability in the region of $0.005 \times 10^{-10}$cm$^2$s$^{-1}$(cm Hg)$^{-1}$ for oxygen, which defines the passage of gas across the membrane when the lumen 2 is evacuated by the analysis instrument.

The particular advantages possessed by the probes of the illustrated type can be summarised as follows:

1. The effective gas permeability of the membrane 10, as defined by its inner layer 6, is low, and the probe thereby avoids the problems of gas-depletion and flow dependence.

2. The inner layer 6 of the membrane 10 is itself significantly thinner than the single-layer membranes of known intravascular probes and confers on the device a very rapid response time.

3. The mechanical support afforded to the membrane layer 6 by the corresponding portion of sheath 5 is sufficient in itself without the need to resort to additional stiffening wires, a sintered metal substrate or a special aperture geometry, all of which feature in prior probe designs.

4. The application of the layer 6 to the entire interior surface of the gas sampling lumen cuts down the passage of ambient gases and water vapour through the walls of the lumen and confers on the device a high signal-to-background ratio.

5. The bio-compatible sheathing 5 and the low-permeability coating 6 permit the catheter 1 to be selected essentially on considerations of its mechanical properties, eg, its flexibility. In particular the illustrated probes are flexible enough to allow the continuous monitoring of gas levels in sick infants.

6. The bilumen construction permits both blood gas sampling and the taking of discreet samples of the blood itself with one and the same probe.

It will be appreciated however that although the invention has been described above in terms of a bilumen probe this need not be the case. Single lumen probes for use in blood gas analysis can be constructed in accordance with the invention to enjoy all of the advantages listed above save number 6.

We claim:

1. A method of manufacturing a device for use in the analysis of absorbed gases in liquids, comprising the steps of taking a flexible plastics material tube with an aperture in its wall; sheathing the exterior surface of at least that portion of the tube which includes said aperture with a layer of bio-compatible gas-permeable material; and coating the interior surface of that area of said sheathing layer which overlies said aperture with a thin layer of gas-permeable material, the permeability of which is significantly less than that of the sheathing layer.

2. A method as claimed in claim 1, in which the entire interior surface of the tube receives the coating of low permeability material.

3. A method as claimed in claim 1 or 2, in which the coating material is polyvinylidene chloride propolymer (PVDC).

4. A method as claimed in claim 1 or 2, in which the coating material is crystalling polytrifluorochloro-ethylene (kel-F).

* * * * *